US012721512B2

(12) United States Patent
Pellissard et al.

(10) Patent No.: US 12,721,512 B2
(45) Date of Patent: Sep. 1, 2026

(54) KIT FOR ACQUIRING A DENTAL REPRESENTATION

(71) Applicant: DENTAL MONITORING, Paris (FR)

(72) Inventors: Thomas Pellissard, Maisons-Alfort (FR); Cédric Lancon, Villers Farlay (FR); Guillaume Ghyselinck, Cantin (FR)

(73) Assignee: DENTAL MONITORING, Paris (FR)

( * ) Notice: Subject to any disclaimer, the term of this patent is extended or adjusted under 35 U.S.C. 154(b) by 176 days.

(21) Appl. No.: 18/277,144

(22) PCT Filed: Feb. 16, 2022

(86) PCT No.: PCT/EP2022/053851
§ 371 (c)(1),
(2) Date: Aug. 14, 2023

(87) PCT Pub. No.: WO2022/175345
PCT Pub. Date: Aug. 25, 2022

(65) Prior Publication Data

US 2024/0164629 A1 May 23, 2024

(30) Foreign Application Priority Data

Feb. 17, 2021 (FR) ...................................... 2101510

(51) Int. Cl.
*A61B 1/24* (2006.01)
*A61B 5/00* (2006.01)

(52) U.S. Cl.
CPC .............. *A61B 1/24* (2013.01); *A61B 5/0077* (2013.01); *A61B 5/6898* (2013.01)

(58) Field of Classification Search
None
See application file for complete search history.

(56) References Cited

U.S. PATENT DOCUMENTS

| | | | | |
|---|---|---|---|---|
| 2,185,508 A * | 1/1940 | Kunze | ...................... | A61B 6/51 396/335 |
| 6,241,798 B1 | 6/2001 | Dimitrov et al. | | |

(Continued)

FOREIGN PATENT DOCUMENTS

| | | |
|---|---|---|
| CN | 109922754 A | 6/2019 |
| EP | 3496592 A1 | 6/2019 |

(Continued)

OTHER PUBLICATIONS

International Search Report corresponding to International Application No. PCT/EP2022/053851 dated May 10, 2022, 7 pages.

(Continued)

*Primary Examiner* — Rodney E Fuller
(74) *Attorney, Agent, or Firm* — Ronald M. Kachmarik; Cooper Legal Group LLC

(57) ABSTRACT

An acquisition kit including: a mobile telephone with an objective lens for acquiring a 2D and/or 3D representation; a holder to which the telephone is fastened, the holder defining an oral aperture to be inserted into the mouth of a user, the objective lens having a view at least partially representing the oral aperture, the view representing at least a first mark selected from: —a categorization mark identifying a category to which a first constitutive component of the holder belongs; and/or —a personalization mark identifying the user and/or pathology of the user and/or dental care professional and/or group of professionals. The kit includes a computer controller programmed to read the first represented mark and to deduce therefrom a first identifier; then record the first identifier and/or prepare and transmit a message to the user and/or dental care professional; and/or to modify the calibration of the telephone.

16 Claims, 8 Drawing Sheets

(56) References Cited

U.S. PATENT DOCUMENTS 6,923,761 B1 8/2005 Dorfman
7,912,257 B2 3/2011 Paley et al.
9,014,440 B2 4/2015 Arumugam et al.
9,152,767 B2 10/2015 Mah
9,770,217 B2 9/2017 Sandholm et al.
9,939,714 B1 4/2018 Matthews
10,032,271 B2 7/2018 Somasundaram et al.
10,136,972 B2 11/2018 Sabina et al.
10,242,443 B2 3/2019 Hsieh et al.
10,463,451 B2 11/2019 Janzadeh et al.
10,467,815 B2 11/2019 Marom et al.
10,504,386 B2 12/2019 Levin et al.
10,588,723 B2 3/2020 Falkel
10,595,966 B2 * 3/2020 Carrier, Jr. ................ G06T 7/13
10,660,728 B2 5/2020 Maraj et al.
10,736,715 B2 8/2020 Salah et al.
10,779,718 B2 9/2020 Meyer et al.
10,842,592 B2 11/2020 Salah et al.
10,849,723 B1 * 12/2020 Yancey .................. A61C 7/002
11,291,532 B2 4/2022 Azernikov et al.
11,532,079 B2 12/2022 Salah et al.
11,599,997 B2 3/2023 Salah et al.
11,638,636 B2 5/2023 Oren-Artzi et al.
2004/0209225 A1 10/2004 Kerrhawe
2007/0160958 A1 7/2007 Belikov et al.
2009/0186655 A1 7/2009 Wernersson
2012/0040305 A1 2/2012 Karazivan et al.
2012/0172685 A1 7/2012 Gilbert
2013/0209954 A1 * 8/2013 Prakash ............. A61B 1/00172 433/29
2013/0244197 A1 9/2013 Tjioe et al.
2014/0005484 A1 1/2014 Charles
2015/0234192 A1 8/2015 Lyons
2016/0374784 A1 12/2016 Joshi
2017/0258420 A1 9/2017 Inglese et al.
2017/0281313 A1 10/2017 Kim
2017/0303857 A1 * 10/2017 Perkins .................. H04N 7/185
2018/0125610 A1 5/2018 Carrier, Jr. et al.
2018/0228359 A1 * 8/2018 Meyer .................... A61C 13/34
2018/0303580 A1 * 10/2018 Salah ..................... A61C 1/088
2019/0026598 A1 * 1/2019 Salah .................. G06F 18/2414
2019/0167115 A1 6/2019 Dorodvand et al.
2020/0060623 A1 2/2020 Sayani et al.
2020/0297205 A1 * 9/2020 Hill .......................... A61B 1/24
2020/0315434 A1 10/2020 Kopelman et al.
2020/0334813 A1 10/2020 Salah et al.
2020/0397273 A1 12/2020 Meyer et al.
2021/0068923 A1 3/2021 Carrier, Jr. et al.
2021/0282634 A1 * 9/2021 Oren-Artzi ............ A61B 1/042
2023/0148852 A1 * 5/2023 Liang ....................... A61B 1/24 348/66
2023/0162360 A1 * 5/2023 Salah ........................ G06T 5/50 348/66
2023/0240820 A1 * 8/2023 Sabina ................... A61B 6/512 348/66
2025/0176815 A1 * 6/2025 Okiyama ........... A61K 31/5383

FOREIGN PATENT DOCUMENTS

EP 3714764 A1 9/2020
FR 3004098 B1 7/2019
JP 4576325 B2 11/2010
JP 2017031794 A 2/2017
JP 2018134418 A 8/2018
KR 101583547 B1 1/2016
WO 2016/066637 A1 5/2016
WO 2016/066642 A1 5/2016
WO 2016/066650 A1 5/2016
WO 2016/066651 A1 5/2016
WO 2016/066652 A1 5/2016
WO 2016/066654 A1 5/2016
WO 2018/029276 A1 2/2018
WO 2020/089248 A1 5/2020
WO 2021/058930 A1 4/2021
WO 2022/008533 A1 1/2022

OTHER PUBLICATIONS

Jun-Yan Zhu, et al., "Unpaired image-to-image translation using cycle-consistent adversarial networks", Mar. 2017, pp. 2223-2232.

Kevis-Kokitsi Maninis et al. "Convolutional Oriented Boundaries: From Image Segmentation to High-Level Tasks," GRIN-DE00135889, Apr. 28, 2017.

Kevis-Kokitsi Maninis et al. "Convolutional Oriented Boundaries: From Image Segmentation to High-Level Tasks," GRIN-DE00135889, Jan. 17, 2017.

*CS Dental Monitoring SAS* v. *Align Technology, Inc.*, Order re Summary Judgment, No. C22-07335 WHA (NDCA, May 16, 2024).

Written Opinion for International Patent Application No. PCT/EP2015/074868 (Feb. 24, 2016).

Written Opinion for International Patent Application No. PCT/EP2015/074895 (Jan. 7, 2016).

Written Opinion for International Patent Application No. PCT/EP2015/074896 (Jan. 12, 2016).

Written Opinion for International Patent Application No. PCT/EP2015/074897 (Jan. 26, 2016).

Written Opinion for International Patent Application No. PCT/EP2019/079565 (Dec. 16, 2019).

International Preliminary Report on Patentability for International Patent Application No. PCT/EP2021/068702 (Jan. 10, 2023).

International Search Report for International Patent Application No. PCT/EP2015/074896 (Dec. 17, 2015).

International Search Report for International Patent Application No. PCT/EP2015/074900 (Dec. 17, 2015).

International Search Report for International Patent Application No. PCT/EP2015/074859 (Dec. 17, 2015).

International Search Report for International Patent Application No. PCT/EP2015/074868 (Dec. 12, 2015).

International Search Report for International Patent Application No. PCT/EP2015/074895 (Dec. 17, 2015).

International Search Report for International Patent Application No. PCT/EP2019/079565 (Dec. 16, 2019).

Prosecution History of the U.S. Pat. No. 11,532,079 to Salah et al.

Prosecution History of the U.S. Pat. No. 11,599,997 to Salah et al.

Declaration of Chandrajit Bajaj, Ph.D., Under 37 C.F.R. § 1.132.

Complaint for Patent Infringement, *Dental Monitoring* v. *Get-Grin Inc.*, Case No. 1-23-cv-00432 (DDE).

Joint Claim Construction Brief, *Dental Monitoring* v. *Get-Grin Inc.*, Case No. 1-22-cv00647 (DDE).

Byju's Math, Cross Sections of Cylinders, available at https://byjus.com/us/math/cross-sections-of-cylinders/.

Certified English Translation of Japanese Publication JP4576325 B2 to Kenji et al.

U.S. Appl. No. 62/417,985 to Carrier, Jr. et al.

EP Application No. 16183461.9 to Dorodvand et al.

"Integral," Merriam-Webster's Collegiate Dictionary (Excerpt), 11th Edition; 2004.

Chinese Office Action from Corresponding Chinese Application No. 202280028773.3, dated May 12, 2026.

* cited by examiner

[Fig 1]
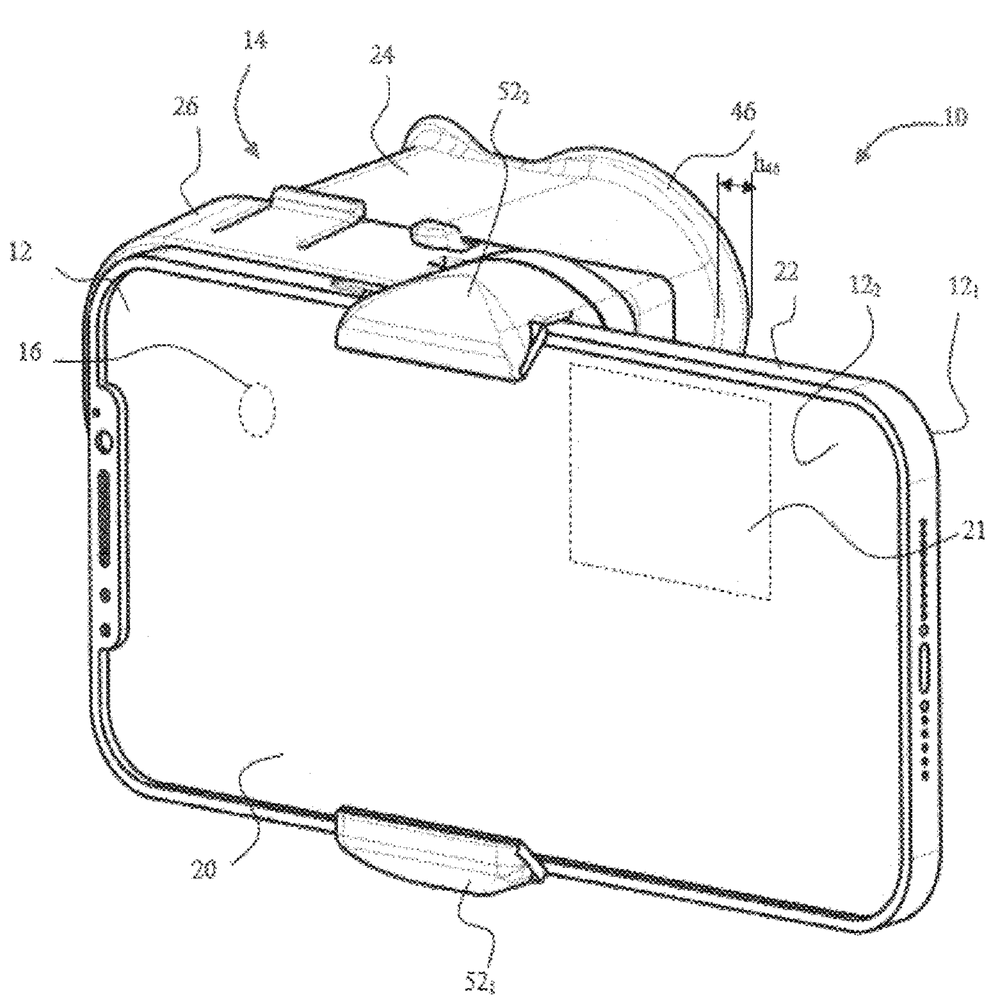

[Fig 2]
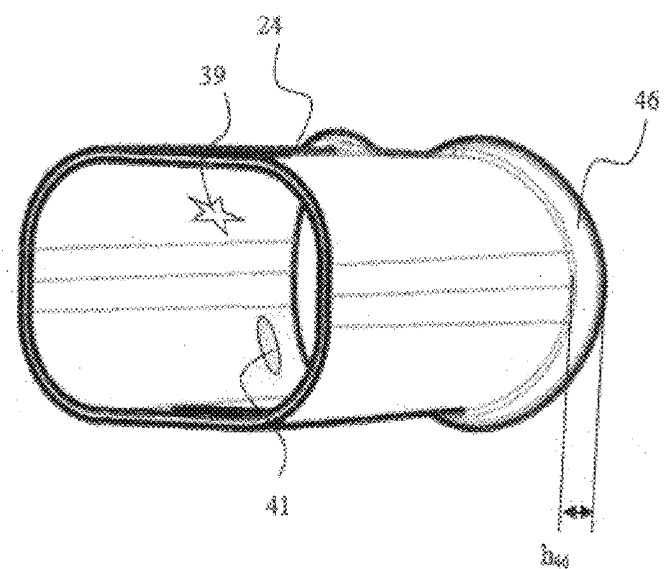
[Fig 3]
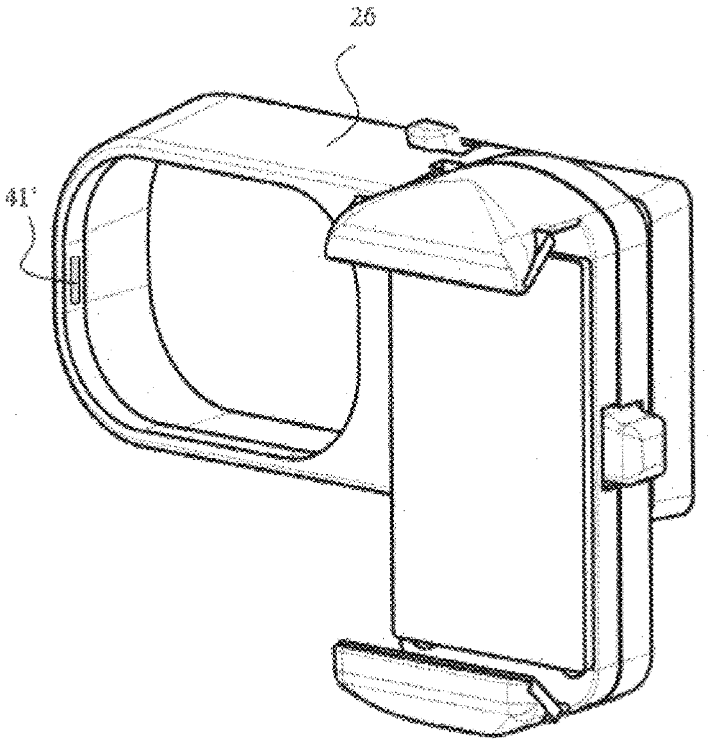

[Fig 4]
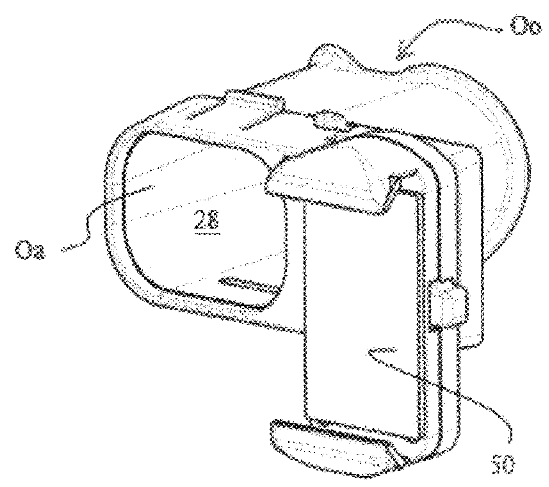
4A
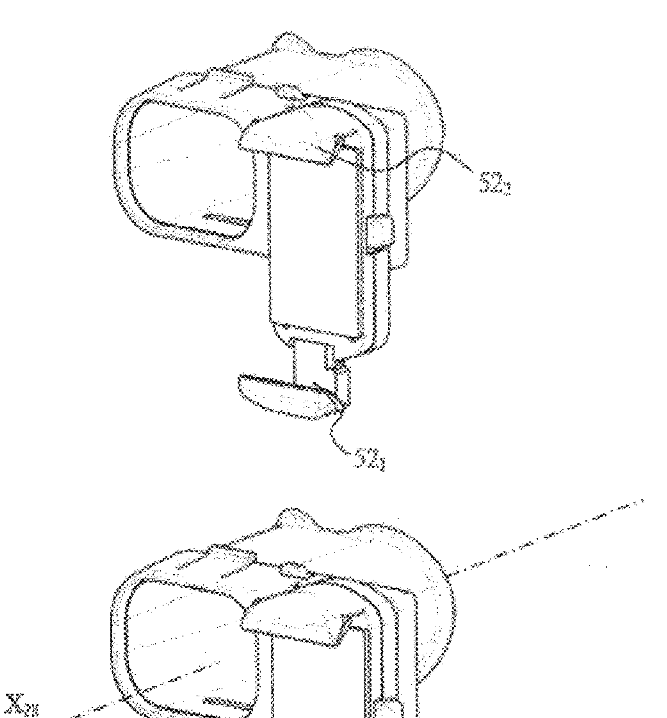
4B
4C

[Fig 5]
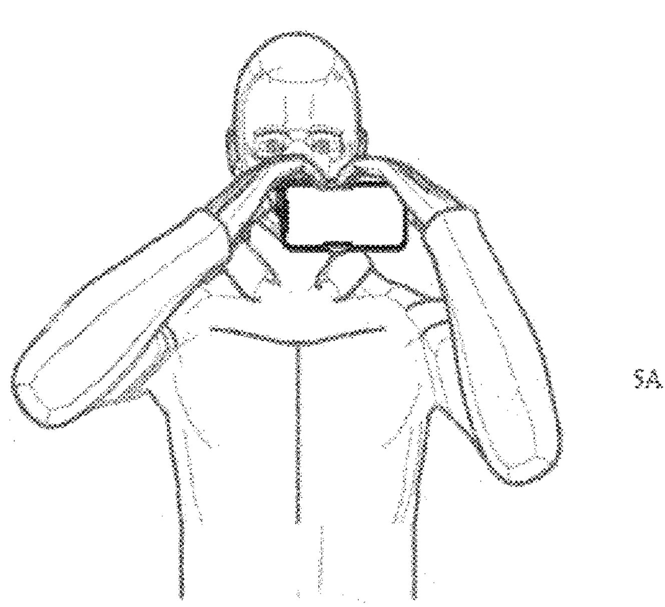
5A
5B

[Fig 6]
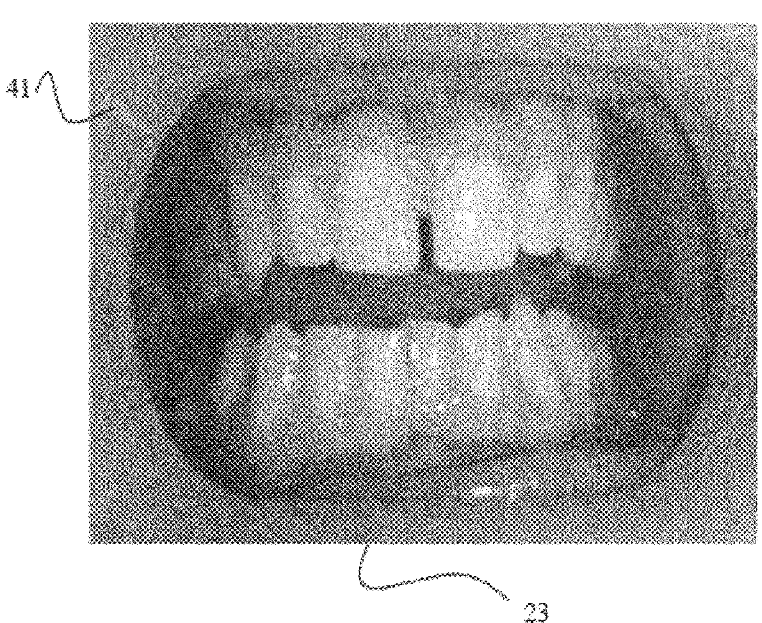

[Fig 7]
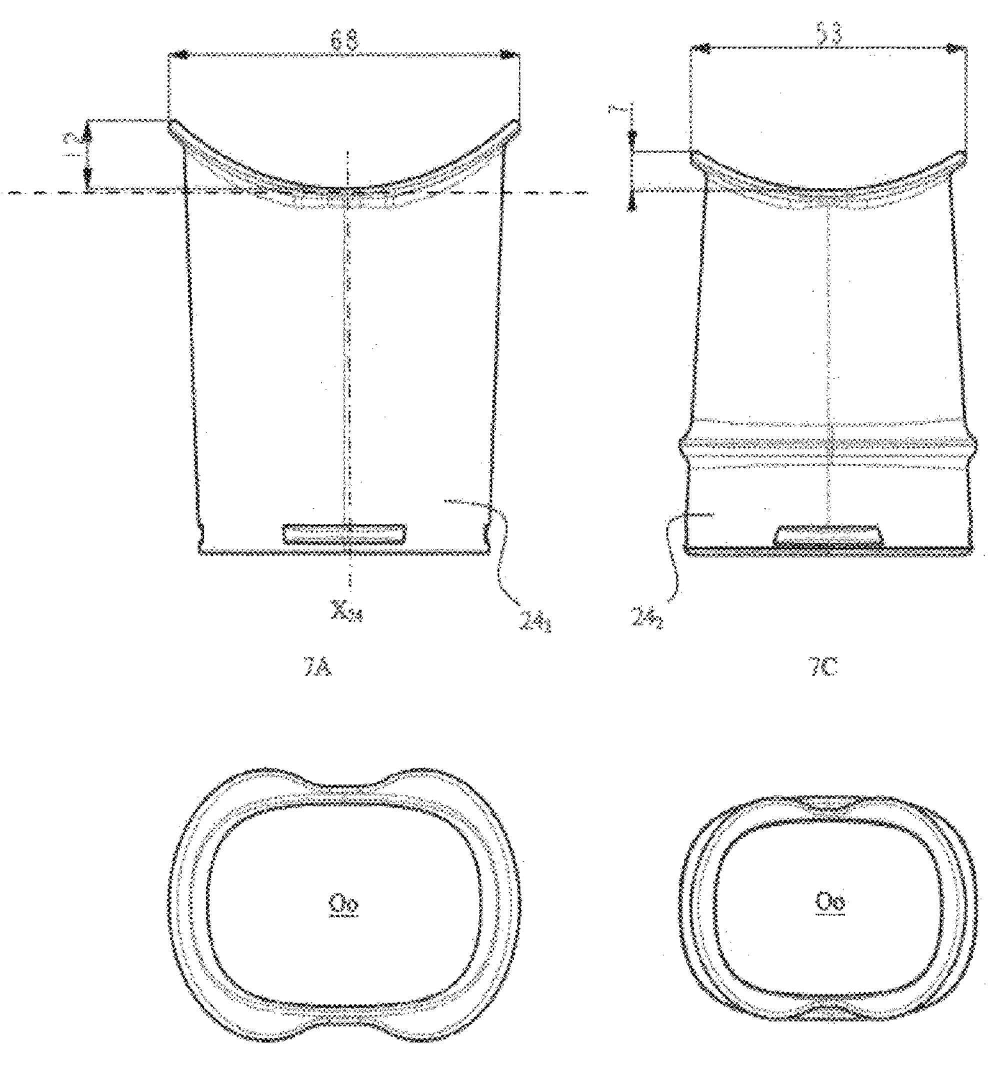

[Fig 8]
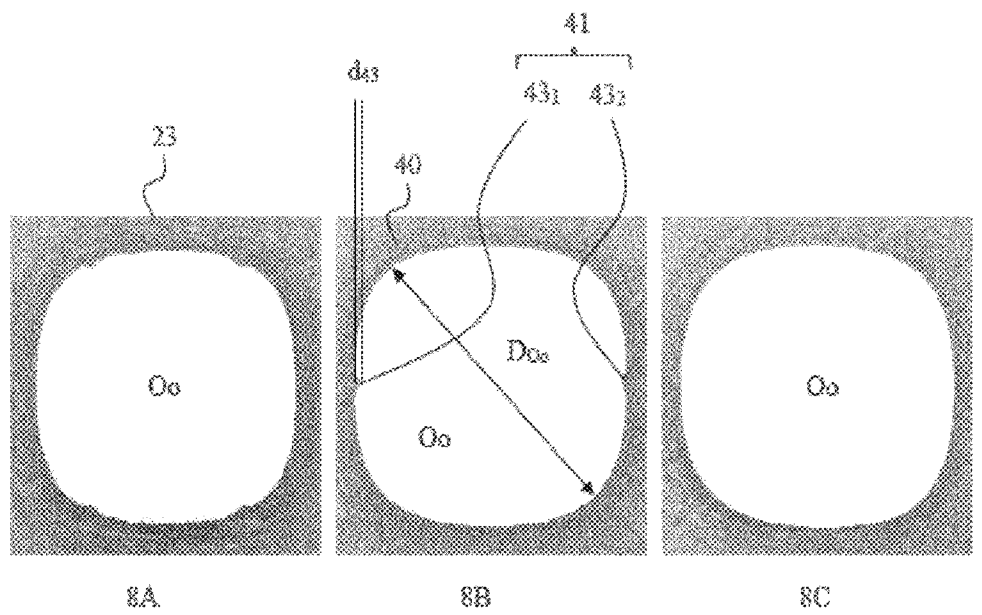
[Fig 9]
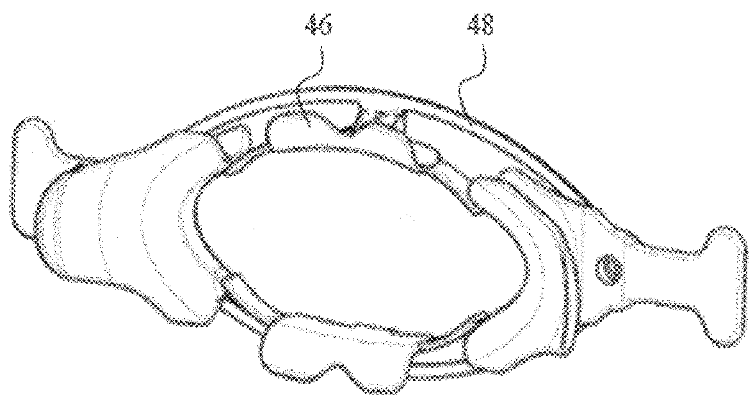

[Fig 10]
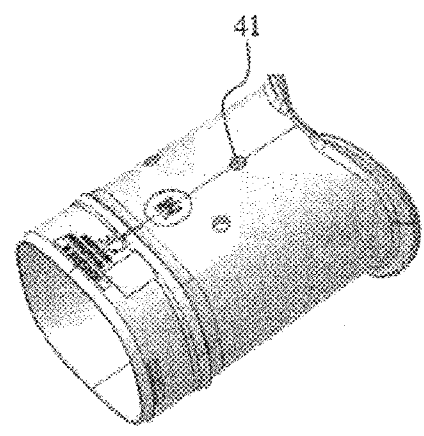
[Fig 11]
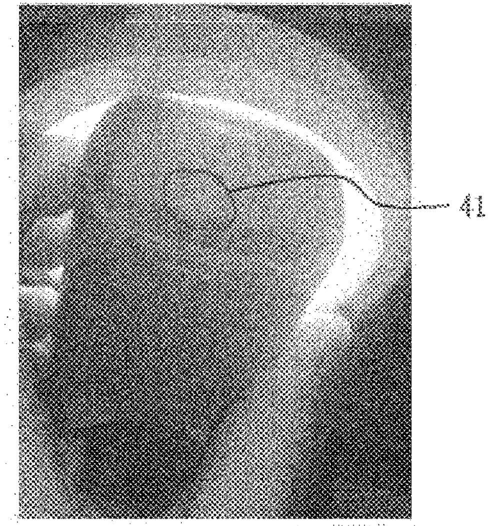

KIT FOR ACQUIRING A DENTAL REPRESENTATION

TECHNICAL FIELD

The present invention relates to an acquisition kit, and in particular for acquiring dental photographs, in particular for implementing a method as described in international application PCT/EP2015/074896.

PRIOR ART

PCT/EP2015/074897 describes an acquisition kit allowing a user to acquire, by way of a mobile telephone, extraoral photographs of their teeth, with their mouth closed or their mouth open, in various orientations.

However, the dimensions of the user's mouth may vary considerably depending on their morphology, in particular depending on their age. If the user does not use an acquisition kit adapted to the dimensions of their mouth, the acquisition is not comfortable and the photographs may be of poor quality.

In addition, it is necessary for the acquisition kit to be approved and for it to comprise only parts that are perfectly compatible with one another, with the model of the mobile telephone and with the calibration of the mobile telephone.

There is therefore a need for an acquisition kit that makes it possible for the user themselves, with the mobile telephone, to acquire 2D representations, such as photographs, or 3D representations, such as three-dimensional models, in occlusal or lateral views, with their mouth open or their mouth closed, and that limits the risk of acquisition with an unsuitable kit.

One aim of the present invention is to at least partially meet this need.

SUMMARY OF THE INVENTION

The invention proposes an acquisition kit comprising:

- a mobile telephone equipped with an optical lens for acquiring a 2D representation and/or a 3D representation;
- a support to which the mobile telephone is attached, preferably removably, the support defining an oral aperture intended to be inserted into the mouth of a user, the optical lens having a view at least partially showing the oral aperture.

According to the invention, said view shows at least one first mark, called "shown first mark", chosen from among:

- a categorization mark identifying, directly or indirectly, a category to which a first component part of the support belongs, and/or
- a personalization mark identifying, directly or indirectly, the user and/or a pathology of the user and/or a dental professional and/or a group of dental professionals, and the kit comprises a computerized controller, preferably integrated into the mobile telephone, programmed so as to 1) read the shown first mark and deduce therefrom a first identifier, and then,
2) record the first identifier, and/or prepare a message on the basis of the first identifier and transmit it to the user and/or to a dental professional, and/or modify the calibration of the mobile telephone on the basis of said first identifier.

As will be seen in greater detail in the remainder of the description, the shown first mark, visible to the optical lens of the mobile telephone, allows the user and/or the controller to check that the configuration of the kit is satisfactory. Such a check may be carried out in real time, thereby making it possible to guide the user and avoid storing 2D or 3D representations that are not compliant with the intended purpose.

In step 2), the controller may in particular display, preferably on the screen of the mobile telephone, information relating to the category identified by the first identifier, for example display the size of the support, thereby allowing the user to check whether this category is satisfactory.

In one embodiment, the controller is programmed so as, after step 1) and prior to step 2), to compare the first identifier with a setpoint so as to determine a score, and then to execute step 2) on the basis of the score, in particular by preparing said message and/or by carrying out said modification of the calibration of the mobile telephone on the basis of the score. No user intervention is advantageously required.

In one preferred embodiment, the shown first mark identifies a category defining a size of the first component part.

Preferably, the shown first mark is a categorization mark arranged such that, in the view observed by the optical lens, it projects toward the inside of the representation of the oral aperture, preferably over a height ($d_{43}$ in FIG. 8) greater than 0.01/10 and less than 1/10 of the largest dimension of the oral aperture. In one preferred embodiment, the categorization mark comprises a local deformation of the oral aperture or a projection protruding from the general contour of the oral aperture.

In one embodiment, the categorization mark comprises one or more projections, the number and/or the shape of the projections, for example the height and/or the width of the projections, directly or indirectly constituting an identifier of said category of said first component part, preferably of a spacer described below, in particular for determining the size thereof.

Preferably, the one or more projections extend in the extension of the oral aperture, and in particular in the plane of the oral aperture when the oral aperture is flat. Advantageously, the representation of the protrusions is substantially identical so that the optical axis, that is to say the axis of the optical lens, is perfectly aligned or slightly offset with respect to the axis of the oral aperture. The identification and interpretation of projections are thereby made easier.

In one embodiment, the support delimits a chamber, preferably of generally tubular shape, opening out via the oral aperture and delimited by a side wall.

The shown first mark, preferably a categorization mark, may in particular be a luminous mark resulting from light passing through the side wall of the support.

The shown first mark, preferably a categorization mark, may be a luminous mark resulting from the illumination of the support from outside the chamber. The luminous mark may be visible by transparency, and for example result from a local reduction in the thickness of the side wall, or from a local modification of its composition or its microstructure. The luminous mark may also result from said illumination through one or more holes formed through the side wall of the support. The one or more holes may in particular be formed through the wall of a spacer.

The shown first mark may also be a color, for example a color specific to the size of a spacer.

Preferably, the setpoint is chosen from the group consisting of:

- a second identifier deduced by virtue of the controller reading a second mark shown in said view,
- information specific to the user,

- a value of a parameter of the mobile telephone, in particular an identifier of the model of the mobile telephone or a calibration parameter of the mobile telephone,
- a normative reference,
- a setpoint derived from said second identifier and/or from said information specific to the user and/or from said value of said parameter of the mobile telephone and/or from said normative reference.

Of course, the setpoint is determined so as to be comparable to the first identifier. For example, if the first identifier identifies that the size of the first component part is a size "S", this size cannot be compared with the name of the user, but can be compared with a size associated with the user, that is to say derived from information specific to the user.

The comparison of the first identifier with the setpoint may consist

- in determining whether there is a difference between the first identifier and the setpoint, the score then being equivalent to "there is a difference" or "there is no difference", or
- in quantifying said difference, the score measuring said difference.

The information specific to the user may in particular relate to the morphology of the user, in particular dimensional information, for example a jaw width. The information specific to the user may be an identifier of the user, for example their name or a number uniquely identifying them.

In one particularly advantageous embodiment, the controller determines the information specific to the user from said view. Preferably, the controller is configured to search in a database referencing a plurality of people for a person compatible with the representation of teeth in said view, and then determine the information specific to the user based on data in relation to said person. In particular, the controller may consider that said person is the user.

The controller may in particular be configured to:

- read a "person identifier" visible in the representation of the mouth in said view,
- compare said person identifier with a plurality of person identifiers each indexing a record of a respective person in the computerized database, and
- identify the user, from among said people, as being the person having a person identifier similar or preferably identical to that read on the representation of the mouth in said view.

The person identifier may for example be provided by reading an oral mark affixed to the mouth, in particular to the teeth of the person in question, for example a mark glued to a tooth of the person.

Preferably, the controller determines information specific to the user, in particular a person identifier, from said view, preferably from the representation of the teeth in said view, in particular on the basis of the shape of one or more teeth, or on the basis of the arrangement of the teeth. For example, the controller may be configured, when the oral aperture is in the user's mouth and user's teeth are visible to the optical lens, to compare the arrangement of said teeth with tooth arrangements of a plurality of people recorded in a database, so as to identify the user from among said people.

The parameter of the mobile telephone may be a parameter of the calibration of the mobile telephone, for example a zoom level or a shutter speed. The parameter of the mobile telephone may be an identifier of the mobile telephone, for example its model, for example the name under which it is marketed, or a serial number uniquely identifying it.

The normative reference may be a regulatory requirement in force in a country or imposed by a company, for example to ensure that the use of the first component part is authorized.

Preferably, the support defines a chamber, preferably of generally tubular shape, opening out, preferably exclusively, via the oral aperture and via an observation aperture through which the optical lens has a view at least partially showing the oral aperture.

The support may consist of a single component part or, preferably, of an assembly of multiple component parts.

It may in particular comprise:

- a spacer opening out via the oral aperture, in particular intended to be inserted between the lips and the teeth of the user of the kit, the spacer possibly comprising a dental retractor defining the oral aperture,
- an adapter attached to the spacer, preferably removably, and defining said chamber with the spacer, the adapter comprising a base to which the mobile telephone is rigidly and preferably removably attached.

In one embodiment, the adapter and the spacer form a one-piece assembly, that is to say that the spacer cannot be detached from the adapter.

The shown first mark may be in particular:

- a categorization mark identifying, directly or indirectly, a category of the adapter and/or
- a categorization mark identifying, directly or indirectly, a category of the spacer, and/or
- a categorization mark identifying, directly or indirectly, a category of the dental retractor.

The first component part may be the spacer, the adapter or the retractor.

A categorization mark may in particular be configured to provide to the controller a geometric characteristic of the first component part, thereby avoiding having to measure it, for example a dimension, and in particular, when it is carried by the spacer, the length of the spacer.

The shown first mark is preferably carried by the first component part.

In one embodiment, said shown first mark, preferably a categorization mark, is carried by the first component part, and the controller is configured to determine the setpoint based on a so-called second identifier provided by a shown second mark, preferably a categorization mark, carried by a second component part of the support, joined removably to the first component part. In particular, the controller is configured to compare first and second identifiers provided by categorization marks carried by two different component parts of the support, and then determine, based on the score obtained, whether the two parts, in particular the spacer and the adapter, are technically compatible, and in particular suitable for being attached to one another, preferably removably.

In one embodiment, the controller is configured to compare a first identifier provided by a categorization mark carried by the adapter or the spacer, and then determine, based on the score obtained, whether the adapter or the spacer is technically compatible with the mobile telephone, and in particular whether the adapter is compatible with attachment of the mobile telephone.

According to some preferred embodiments:

- the first identifier designates a spacer category, said setpoint designates an adapter category, and the controller is programmed to deduce said first identifier from a categorization mark carried by the spacer and, preferably, to deduce said setpoint from a categorization mark carried by the spacer, and then, preferably, to check, based on the score, the compatibility between the spacer and the adapter, for example to check that they have compatible dimensions, or that their respective manufacturers have validated the combination of the adapter and the spacer;

the first identifier designates an adapter category, the setpoint designates a mobile telephone category, and the controller is programmed to deduce said first identifier from a categorization mark carried by the adapter, and then, preferably, to check, based on the score, the compatibility between the mobile telephone and the adapter;

the first identifier designates a spacer category, the setpoint designates a value of a parameter of the calibration of the mobile telephone, and the controller is programmed to deduce said first identifier from a categorization mark carried by the adapter, and then, preferably, to check, based on the score, the compatibility between the calibration of the mobile telephone for acquiring the 2D and 3D representation and the spacer. Preferably, the controller is programmed to modify the calibration of the mobile telephone on the basis of said score, in particular in the event of incompatibility;

the first identifier designates a support category, in particular spacer category, the setpoint designates a support category, in particular spacer category, derived from the information specific to the user, and the controller is programmed to deduce said first identifier from a categorization mark carried by the support, in particular the spacer, and preferably to determine, based on the score obtained, whether the support, in particular the spacer, is technically compatible with the user, and in particular determine whether the size of the support, in particular of the spacer, is suitable for the morphology of the user; advantageously, it is thus possible to check the compatibility between the spacer and the user, for example to check that the spacer is suitable for the age and/or for the size of the user;

the first identifier designates a support category, in particular spacer or adapter category, the setpoint designates a prescription set by a state or a company, and the controller is programmed to deduce said first identifier from a categorization mark carried by the support, in particular the spacer or the adapter, and then, preferably, to check, based on the score, the compatibility between the support, in particular the spacer or the adapter, and said prescription.

An acquisition kit according to the invention may in particular comprise one or more of the following preferred features:

the acquisition kit comprises, in addition to the spacer attached to the adapter, at least one other spacer able to be joined to the adapter, different from the spacer attached to the adapter and carrying another shown mark, in particular a categorization mark, different from that carried by the spacer attached to the adapter;

preferably, said other spacer has a length identical to the spacer attached to the adapter, thereby advantageously allowing identical calibration of the mobile telephone regardless of the spacer that is used;

the spacer comprises

- a body of tubular general shape defining the oral aperture and
- a distal rim, preferably integral with the body, extending outwardly from the body and shaped to be inserted between the user's lips and teeth.

The invention also relates to a method for acquiring a 2D or 3D representation by way of an acquisition kit according to the invention, said method comprising the following steps:

a) the user partially inserting the support into the user's mouth such that the optical lens of the mobile telephone has a view of the user's teeth through the oral aperture, the support preferably spreading the user's lips so as to reveal said teeth;

b) preferably the user activating the mobile telephone so as to acquire said 2D or 3D representation;

c) optionally, modifying the positioning of the oral aperture relative to the user, for example by rotation about the user, and then returning to step b);

d) optionally, preferably the user dismantling the acquisition kit;

(e) optionally, washing and/or disinfecting the spacer, or even only the spacer.

According to the invention, at at least one checking time, the controller executes a series of steps 1) and 2). Preferably, it informs the user of said score in real time, preferably via the mobile telephone.

If the check does not require the optical lens to have a view of the patient's teeth, for example to check the compatibility between the spacer and the adapter, the checking time may be at any time before step d), preferably before step b), preferably before step a).

Preferably, the user modifies the kit on the basis of the information received from the controller. In one embodiment, the controller modifies the calibration of the mobile telephone. In one embodiment, the controller prohibits the acquisition of a 2D or 3D representation if the score obtained is unsatisfactory.

Preferably, at least one so-called representation facing the user and at least one so-called representation to the right or to the left of the user and/or preferably at least one so-called representation with the mouth open and at least one so-called representation with the mouth closed are acquired.

Definitions

The "service position" is the position in which the oral aperture extends into the user's mouth, as illustrated in FIG. 5.

The "mouth closed" position is the occlusion position in which the user's upper and lower teeth are in contact. A "mouth open" position is a position in which the user's upper and lower teeth are not in contact, preferably the position with the mouth fully open.

A "mobile telephone" is the name given to an iPhone®-type device. Such a device typically weighs less than 500 g. It is equipped with a camera allowing it to take films or photographs, or even a scanner allowing it to acquire three-dimensional digital models, through an optical lens. A mobile telephone is also capable of exchanging data with another device more than 500 km away from the mobile telephone.

The mobile telephone makes it possible to acquire 2D or 3D "extraoral" representations, that is to say without the lens of the mobile telephone being inserted into the user's mouth.

The optical lens of the mobile telephone "has a view" on an object when the triggering of the acquisition of a 2D or 3D representation leads to the recording of a 2D or 3D representation that shows this object.

The "acquisition configuration", or "calibration", consists of the set of calibration parameters of the mobile telephone that determine the conditions for the acquisition of the 2D or 3D representations through the optical lens of the mobile telephone. A calibration parameter is a parameter intrinsic to the acquisition device (unlike its position and its orientation) the value of which influences the acquired 2D or 3D representation. For example, diaphragm aperture is a calibration parameter that modifies the depth of field of an image. Exposure time is a calibration parameter that modifies the brightness (or "exposure") of an image. Focal length is a calibration parameter that modifies viewing angle, that is to say the degree of "zoom". "Sensitivity" is a calibration parameter that modifies the reaction of the sensor of an acquisition device to incident light. Preferably, the calibration parameters are chosen from the group formed by diaphragm aperture, exposure time, focal length and sensitivity.

An "acquisition position" is a position in which the optical lens of the mobile telephone has an at least partial, preferably complete view of the oral aperture through the observation aperture and the acquisition aperture.

A "2D representation" and a "3D representation" are two-dimensional or three-dimensional digital objects, respectively, acquired by a mobile telephone, extraorally, through the optical lens of the mobile telephone. The "2D representations" acquired by the mobile telephone are images, and in particular conventionally photographs and films. The "3D representations" acquired by the mobile telephone are three-dimensional digital models, or "3D models".

An "image" is understood to mean a two-dimensional image, such as a photograph. An image is formed from pixels. A "film" is considered to be a set of photographs.

A 3D model consists of a set of voxels.

An "acquirable" 2D or 3D representation is a representation that is not yet recorded in the mobile telephone, for example an image shown on the screen of the mobile telephone. An "acquired" 2D or 3D representation is a representation recorded in the mobile telephone and/or in a remote computer in communication with the mobile telephone.

The controller is "configured" or "programmed" for an action when it comprises a computer program comprising program code instructions for carrying out said action when said program is executed by a computer.

It is considered that one element integral with another is "attached" rigidly to this other element.

A "database" is a computerized database, for example a relational database.

A "user" is understood to mean a person who uses a kit according to the invention to acquire a 2D or 3D representation of at least some of their teeth, whether or not this person is ill, or whether or not this person is undergoing orthodontic treatment.

A "dental professional" is understood to mean a dentist, orthodontist or orthodontic laboratory.

A "retractor", or "dental retractor", is a device intended to roll up the lips. It has an upper rim and a lower rim, and/or a right rim and a left rim, extending around a retractor aperture and intended to be inserted between the teeth and the lips. In the service position, the user's lips bear against these rims, so that the teeth are visible through the retractor aperture. A retractor thus makes it possible to observe the teeth without being obstructed by the lips. Retractors are described for example in PCT/EP2015/074896, U.S. Pat. No. 6,923,761, or US 2004/0209225.

A "marked part" is a component part of the support that carries a shown mark.

An "identifier" of an object, or "designating" an object, is information made available by reading a shown mark and that makes it possible to identify this object alone ("directly identifying the object") or by using additional information ("indirectly identifying the object" or "indirect identifier"). In both cases, it is said that the identifier is "deduced" from the shown mark.

An identifier may be for example an alphanumeric code, a color, a texture or a shape of the marked part. The shown mark must be read in order to provide an identifier. For example, a barcode may be read in order to provide an alphanumeric code. This alphanumeric code is an identifier in that it is associated, directly or indirectly, with an object, for example in a database.

Additional information is the information needed to identify the object based on the indirect identifier. The additional information may be for example a correspondence table establishing a link between the indirect identifier and a direct identifier of the object. For example, a categorization mark may provide a serial number (indirect identifier) and this serial number may be associated with a spacer (or adapter) size (indirect identifier) by way of a correspondence table giving, for each serial number, the size of the spacer (or adapter).

An identifier "deduced" from a shown mark may be a code read by the controller or information determined based on this code, for example by consulting a computerized database establishing an association between said code and said identifier.

The setpoint is said to be "derived from the second identifier and/or from said information specific to the user and/or from said parameter of the mobile telephone and/or from said normative reference" in that it is determined based on said second identifier and/or on said information specific to the user and/or on said parameter of the mobile telephone and/or on said normative reference, directly or indirectly, for example, by consulting a computerized database establishing an association between the derived setpoint, on the one hand, and said second identifier and/or said information specific to the user and/or said parameter of the mobile telephone and/or said normative reference, on the other hand.

An object has characteristics that allow it to be classified into one or more "categories". For example, a category may group together all objects having one and the same size, for example S, M, or L. The spacers in the category "S", "M" and "L" may for example be all spacers that have an oral aperture whose length, measured in the horizontal direction in the service position, is between 35 and 45 mm, between 45 mm and 55 mm, and between 55 and 65 mm, respectively.

Deep-learning algorithms are deep-learning devices that are well known to a person skilled in the art. They comprise "neural networks" or "artificial neural networks".

A person skilled in the art will be able to choose a neural network, depending on the task to be performed. In particular, a neural network may be chosen from among:

- networks specializing in image classification, called "CNN" ("convolutional neural network"), for example AlexNet (2012), ZF Net (2013), VGG Net (2014), GoogleNet (2015), Microsoft ResNet (2015), Caffe: BAIR Reference CaffeNet, BAIR AlexNet, Torch: VGG_CNN_S, VGG_CNN_M, VGG_CNN_M_2048, VGG_CNN_M_1024, VGG_CNN_M_128, VGG_CNN_F, VGG ILSVRC-2014 16-layer, VGG ILSVRC-2014 19-layer, Network-in-Network (Imagenet & CIFAR-10), Google: Inception (V3, V4), networks specializing in locating and detecting objects in an image, Object Detection Networks, for example R-CNN (2013), SSD (Single Shot MultiBox Detector: Object Detection network), Faster R-CNN (Faster Region-based Convolutional Network method: Object Detection network), Faster R-CNN (2015), SSD (2015), RCF (Richer Convolutional Features for Edge Detection) (2017), SPP-Net, 2014, OverFeat (Sermanet et al.), 2013, GoogleNet (Szegedy et al.), 2015, VGG-Net (Simonyan and Zisserman), 2014, R-CNN (Girshick et al.), 2014, Fast R-CNN (Girshick et al.), 2015, ResNet (He et al.), 2016, Faster R-CNN (Ren et al.), 2016, FPN (Lin et al.), 2016, YOLO (Redmon et al.), 2016, SSD (Liu et al.), 2016, ResNet v2 (He et al.), 2016, R-FCN (Dai et al.), 2016, ResNeXt (Lin et al.), 2017, DenseNet (Huang et al.), 2017, DPN (Chen et al.), 2017, YOLO9000 (Redmon and Farhadi), 2017, Hourglass (Newell et al.), 2016, MobileNet (Howard et al.), 2017, DCN (Dai et al.), 2017, RetinaNet (Lin et al.), 2017, Mask R-CNN (He et al.), 2017, RefineDet (Zhang et al.), 2018, Cascade RCNN (Cai et al.), 2018, NASNet (Zoph et al.), 2019, CornerNet (Law and Deng), 2018, FSAF (Zhu et al.), 2019, SENet (Hu et al.), 2018, ExtremeNet (Zhou et al.), 2019, NAS-FPN (Ghiasi et al.), 2019, Detnas (Chen et al.), 2019, FCOS (Tian et al.), 2019, CenterNet (Duan et al.), 2019, EfficientNet (Tan and Le), 2019, AlexNet (Krizhevsky et al.), 2012 networks specializing in image generation, for example Cycle-Consistent Adversarial Networks (2017), Augmented CycleGAN (2018), Deep Photo Style Transfer (2017), FastPhotoStyle (2018), pix2pix (2017), Style-Based Generator Architecture for GANs (2018), SRGAN (2018).

The above list is non-limiting.

Training a neural network consists in confronting it with a learning base containing information about the two types of object that the neural network must learn to "match", that is to say connect to one another.

Training may be carried out based on a learning base consisting of records each comprising a first object of a first type and a corresponding second object of a second type.

As an alternative, training may be carried out based on a learning base consisting of records each comprising either a first object of a first type or a second object of a second type, each record however comprising information relating to the type of object that it contains. Such training techniques are for example described in the article by Zhu, Jun-Yan, et al. *"Unpaired image-to-image translation using cycle-consistent adversarial networks."*

Training the neural network with these records teaches it to deliver, from any object of the first type, a corresponding object of the second type.

The quality of the analysis carried out by the neural network depends directly on the number of records in the learning base. Preferably, the learning base contains more than 10 000 records.

A measure of the difference between these two objects is called a "match" or "fit" between two objects. A match or a fit is greatest ("best fit") when it makes it possible to minimize said difference.

Two images, for example a photograph and a view of a 3D model, that exhibit a maximum match show substantially one and the same object in the same way. In other words, the representations of the object in these two images are able to be substantially superimposed.

A 3D model exhibits a maximum match with an image, in particular a photograph, when it has a view that exhibits a maximum match with said image.

The determination of the match may result from the comparison between two images. Preferably, this comparison itself results from the comparison of two corresponding maps. A measure of the difference between two maps or between two images is conventionally called a "distance". A map may show discriminating information, which is characteristic information that may be extracted from an image ("image feature"), conventionally by computerized processing of this image. The discriminating information is preferably chosen from the group consisting of contour information, color information, density information, distance information, gloss information, saturation information, information on reflections and combinations of these forms of information. The discriminating information is preferably contour information.

"Metaheuristic" methods are known optimization methods. They are preferably chosen from the group formed by evolutionary algorithms, preferably chosen from among evolution strategies, genetic algorithms, differential-evolution algorithms, estimation of distribution algorithms, artificial immune systems, path relinking, shuffled complex evolution, simulated annealing, ant-colony-optimization algorithms, particle-swarm-optimization algorithms, taboo search, and the GRASP method;

the kangaroo algorithm, the Fletcher-Powell method, the noise method, stochastic tunneling, random-restart hill climbing, the cross-entropy method, and hybrid methods combining the abovementioned metaheuristic methods.

Unless indicated otherwise, the qualifiers used to define positions or orientations in space, such as "horizontal", "vertical", "bottom", "top", "upper", "lower", "right" or "left" are defined, for clarity purposes, with reference to a service position observed by a user, having their head upright and having their lips arranged around the oral aperture. For example, a vertical axis is an axis that is vertical in the service position.

Unless indicated otherwise, the qualifiers "outer" and "inner" refer to volumes or to closed contours, to designate an element outside the volume, for example outside a chamber, or outside the closed contour. For example, the outer surface of a tubular body is the surface that is exposed to the outside of the tubular body.

The adjectives "first" and "second" are used only for clarity purposes. In particular, the presence of a shown first mark does not imply the presence of other shown marks.

For the sake of clarity, an axis or a direction that extends horizontally and perpendicularly to the general plane of the oral aperture in the service position is referenced $X_i$, "i" being an index referring to a part concerned by this axis or this direction. For the user, axes $X_i$, are therefore front-to-rear axes.

The axis of an aperture is the axis that passes through the center thereof, perpendicular to the general plane of the aperture.

First and second straight lines are said to be perpendicular to one another when first and second planes perpendicular to said first and second straight lines, respectively, are perpendicular to one another.

"Comprise", "have" and "exhibit" should be interpreted broadly and without limitation, unless indicated otherwise.

BRIEF DESCRIPTION OF THE FIGURES

Other features and advantages of the invention will become more clearly apparent on reading the detailed description that follows and on examining the appended drawing, in which:

FIG. 1 shows a kit according to the invention, in perspective, in the assembled position;

FIG. 2 shows the spacer of the kit from FIG. 1, in perspective;

FIG. 3 shows, in perspective, the adapter of the kit from FIG. 1;

FIG. 4 illustrates, for the kit from FIG. 1, the spreading movement of the first jaw, from the close position (FIG. 4A) to the spread position (FIG. 4B), passing through an intermediate position (FIG. 4C);

FIG. 5 schematically illustrates the service position, the user being seen from the front (FIG. 5A) and from the side (FIG. 5B);

FIG. 6 shows a view observed by the lens of the mobile telephone;

FIG. 7 shows a first spacer seen from above (FIG. 7A) and from the front (FIG. 7B), and a second spacer, of one and the same acquisition kit, seen from above (FIG. 7C) and from the front (FIG. 7D); FIG. 7 provides dimensional indications;

FIG. 8 shows photographs taken in the acquisition position with first (FIG. 8A), second (FIG. 8B), and third (FIG. 8C) spacers;

FIG. 9 shows one example of a retractor;

FIG. 10 illustrates one example of a spacer comprising a shown mark generated by the passage of light through holes formed in the side wall of said spacer;

FIG. 11 illustrates one example of a shown mark visible, by transparency, through the wall of a spacer.

In the various figures, identical or similar members have been designated with identical references.

The figures are provided for illustrative purposes. They are not limiting.

DETAILED DESCRIPTION

The kit 10 shown in FIG. 1 comprises a mobile telephone 12 and a support 14.

Mobile Telephone

Any conventional mobile telephone may be used.

The mobile telephone 12 is a personal device, conventionally of substantially parallelepipedal shape, conventionally comprising a camera.

A mobile telephone conventionally has:

a front face $\mathbf{12}_1$ equipped with at least one optical lens 16 and, preferably, a flash, a rear face $\mathbf{12}_2$ having a screen 20, and an edge 22, defining the thickness of the telephone and joining the front and rear faces.

The screen 20 covers substantially the entire rear face. It serves as interface for the user. In particular, it allows said user to visualize what the optical lens 16 "sees", that is to say the "view" of the optical lens. Preferably, the screen 20 is a touch screen and makes it possible to control functions of the mobile telephone.

The optical lens 16 conventionally has an optical axis perpendicular to the front face, and makes it possible to acquire 2D representations 23, as in FIGS. 6 and 8, or even 3D representations. In particular, it makes it possible to acquire color photographs, and/or infrared photographs. Infrared photographs advantageously make it possible to display the teeth with excellent contrast.

The mobile telephone 12 is attached, preferably removably, to the support 14.

In one preferred embodiment, the mobile telephone incorporates a controller 21, described in more detail below.

Support

The support 14 has a dual function. It makes it possible, simultaneously, to spread the user's lips so as to reveal the teeth, and to facilitate the positioning and the orientation of the mobile telephone in relation to the teeth.

It comprises a spacer 24, shown in isolation in FIG. 2, and an adapter 26, shown in isolation in FIG. 3, which, after being joined and in the preferred embodiment, together define a chamber 28 (see FIG. 4) opening out via an oral aperture Oo, on the one hand, and via an observation aperture Oa facing the lens 16 of the mobile telephone 12, on the other hand, which apertures are preferably coaxial. Preferably, the chamber 28 opens out to the outside only via the oral aperture Oo and observation aperture Oa and, more preferably, the mobile telephone 12 closes off the observation aperture Oa. Advantageously, the brightness of the external environment does not influence the acquisition of 2D or 3D representations (images or 3D models) by the mobile telephone.

The chamber 28 is preferably substantially tubular, preferably rectilinear, with an axis $X_{28}$, and the chamber 28 preferably has the shape of a cylindrical or frustoconical tube, for example with a circular, oval or polygonal cross section, for example a rectangular cross section. The cross section of the chamber, that is to say in a sectional plane perpendicular to the axis $X_{28}$, may be constant or variable along the axis $X_{28}$.

The length of the chamber 28, measured along the axis $X_{28}$, is preferably greater than 3 cm, preferably greater than 5 cm, preferably greater than 7 cm, preferably greater than 8 cm and/or less than 25 cm, preferably less than 20 cm, preferably less than 15 cm, preferably less than 10 cm.

Preferably, in a portion of the chamber extending over more than 70%, more than 80%, more than 90%, more than 95%, more than 99%, preferably 100% of the length of the chamber, the spacer has an inner surface that is smooth to the touch, free from projecting edges and/or free from receding edges, and in particular free from the projections described below, a portion of the chamber being a fraction of the chamber delimited by two planes perpendicular to the axis $X_{28}$.

In one embodiment, the adapter 26 and the spacer 24 form a one-piece assembly, the adapter 26 being rigidly and permanently attached to the spacer 24, or even being integral with the spacer.

The adapter 26 is preferably rigidly and removably attached to the spacer 24. Advantageously, the adapter 26 may be used for multiple spacers. Also advantageously, the spacer 24 may be cleaned or sterilized independently of the adapter.

Spacer

The spacer 24, preferably of tubular general shape, opens out on one side via the oral aperture Oo and, on the opposite side, facing the observation aperture Oa. Its function is to define a spacing between the mobile telephone attached to the adapter 26 and the oral aperture Oo and also, preferably, a predefined orientation of the mobile telephone with respect to the oral aperture. Advantageously, in the service position, the representations (images or 3D models) acquired by the mobile telephone 12 through the optical lens 16 are thus acquired at a predetermined distance from the user's teeth and with a predefined orientation. Preferably, the spacer 24 is configured such that this spacing and this orientation are constant.

The spacer 24 preferably comprises an outwardly extending distal rim 46, at the periphery of the oral aperture Oa and from the outer surface of the body 40, able to be inserted between the user's lips and teeth. Advantageously, the lips may thus be separated so as not to close off the oral aperture Oa. The distal rim 46 also facilitates retention of the spacer 24 in the user's mouth.

Preferably, the distal rim 46 is flat, that is to say has the shape of a blade, preferably with a constant thickness.

Preferably, the distal rim 46 extends substantially radially with respect to the axis of the oral aperture Oo, that is to say in a plane perpendicular to this axis.

More preferably, the distal rim extends in the extension of the oral aperture. The distal rim 46 may surround the body 40 fully or partially. Preferably, it comprises a right portion and a left portion that are intended to bear on the right and left corners of the lips of the user.

The distal rim 46 may be interrupted, as in the embodiment shown, or may comprise a notch, so as to leave free the frenum present at the upper and lower arches of the user. The interruption or the notch also make it possible to move the spacer 24 in the user's mouth, in particular to perform rotations about the dental arches so as to acquire photographs or 3D models in lateral views. The notch may for example have a triangular, rounded or rectangular shape.

The maximum height $h_{46}$ of the distal rim 46 is preferably greater than 1 mm, greater than 2 mm, greater than 3 mm, and/or less than 10 mm, 8 mm, or 6 mm.

The distal rim 46 is preferably integral with the tubular body of the spacer 24. The distal rim may alternatively be defined by a dental retractor 48 (FIG. 9) attached removably to the tubular body of the spacer.

More preferably, the spacer 24 is made in one piece. Its manufacturing cost is advantageously thereby limited.

Adapter

The function of the adapter 26 is to removably attach the mobile telephone to the support 14 and to position it in an acquisition position allowing the lens 16 of the mobile telephone 12 to observe the oral aperture Oa through the observation aperture Oo. Preferably, the adapter 26 is configured such that this position is able to be modified.

The mobile telephone 12 may be attached to the adapter 26, for example, with one or more elastic bands, one or more straps, one or more self-gripping bands, one or more clips, one or more screws, a flap, for example mounted so as to rotate on the base of the adapter and able to be locked in a position in which it clamps the mobile telephone 12, jaws, one or more suction cups or one or more magnets. The mobile telephone may also be inserted into a shell, a cover or a case, attached to a base of the adapter. This list of examples is not limiting.

More preferably, the adapter 26 is configured to allow the attachment of various mobile telephones, and in particular mobile telephones having different dimensions.

In one preferred embodiment, the mobile telephone 12 is clamped to the adapter 26. In particular, and preferably, as illustrated in FIG. 4, the adapter 26 comprises a base 50, a first jaw 521 and a second jaw 522, opposite the first jaw, which jaws are configured to trap and clamp the mobile telephone 12, preferably by pressing on the edge 22 of the mobile telephone.

Shown Mark

Preferably, at least one region of the chamber 28 that is visible in the view observed by the optical lens 16 carries a personalization mark 39 and/or a categorization mark, referenced 41 in FIGS. 2 and 6, in which the categorization mark is carried by the spacer, or referenced 41' in FIG. 3, in which the categorization mark is carried by the adapter.

The personalization mark 39 is preferably configured to provide to the controller 21:

- an identifier of the user, for example their name, and/or of a group to which the user belongs, for example indicating whether the marked part (that is to say the spacer 24 and/or the adapter 26) is intended for a man or a woman, an adult or a child; or
- an identifier of a dental professional's practice and/or of a company associated with a marked part, for example an identifier of a particular orthodontist or of a dental company, for example a group of dental professionals; or
- an identifier of a possible pathology or orthodontic treatment of the user.

In one embodiment, the personalization mark shows a design or trademark or a three-dimensional shape.

The categorization mark 41' or 41 is configured to provide to the controller 21 an identifier of an adapter 26 category or spacer 24 category, respectively. It therefore does not identify a characteristic of a natural or legal person associated with a marked part, such as a personalization mark carried by the marked part, but a characteristic of the marked part.

The personalization mark 39 and/or the categorization mark 41 or 41' is (are) shown in the acquirable or acquired 2D or 3D representations.

The personalization mark and/or the categorization mark may be carried by a support part attached, preferably removably, to the marked part. This support part may be attached by any known means, in particular by way of one or more clips, screws, Velcro® self-gripping tapes, elastic bands, magnets, hooks, bolts, straps, suction cups, or an adhesive material. The support part may in particular be an adhesive label or a token.

The personalization mark and/or the categorization mark may also be inscribed, or engraved, on the marked part, preferably on the spacer. The inscription may be made for example by way of a pencil, for example by way of an indelible marker, in particular on a cardboard spacer, or by pad printing. In one embodiment, the inscription is erasable.

The personalization mark 39 and/or the categorization mark 41 may comprise or consist of, for example, a luminous mark, a colored marker, alphanumeric characters, a design, a geometric or non-geometric pattern, for example a QR code or a barcode, a particular microstructure or region made of a material different from the material of the marked part carrying them.

The personalization mark 39 and/or the categorization mark 41 may for example represent more than 0.1%, more than 0.5%, more than 1%, more than 3% and/or less than 95%, less than 90%, less than 50%, less than 20%, less than 10% of the surface area of the marked part carrying them.

The personalization mark 39 and/or the categorization mark 41 are preferably non-removable. Preferably, they are integral with the marked part.

Preferably, the personalization mark 39 and/or the categorization mark 41 do not comprise any receding edges capable of retaining dirt. Cleaning or sterilization are therefore more effective as a result. Preferably, the personalization mark 39 and/or the categorization mark 41 do not comprise any projecting edges likely to injure the user, in particular when they are close to the oral aperture.

Preferably, the personalization mark 39 and/or the categorization mark 41 is (are) arranged such that, in the view observed by the lens 16, it/they extends/extend at least partially through the oral aperture. As illustrated in FIG. 8, to prevent it/them from masking the teeth in a detrimental manner, it/they preferably extends/extend from the rim of the oral aperture over a distance $d_{43}$:

- less than 10/100, preferably less than 5/100, preferably less than 3/100, preferably less than 2/100, preferably less than 1.5/100 and/or preferably greater than 0.1/100, preferably greater than 0.5/100, preferably greater than 0.7/100, of the largest dimension $D_{Oo}$ of the oral aperture, and/or
- less than 10 mm, preferably less than 5 mm, preferably less than 3 mm, preferably less than 2 mm, preferably less than 1 mm and/or greater than 0.1 mm.

In one embodiment, the personalization mark 39 and/or the categorization mark 41 extend in the extension of the distal rim.

In one embodiment, the categorization mark comprises or consists of a local deformation of the oral aperture or a projection protruding from the general contour of the oral aperture.

The categorization mark may be formed by an excess thickness, for example by a bead or a pad of material, or by an under-thickness, for example by a groove, a depression, a hole, or a notch, in the wall that delimits the chamber, over all or part of its length, preferably only at the oral aperture.

In one preferred embodiment illustrated in FIG. 8, the spacer comprises a categorization mark 41 in the form of one or more projections 43 (referenced $\mathbf{43}_1$ and $\mathbf{43}_2$ in FIG. 8B) that are visible in photographs acquired by the mobile telephone and that preferably extend into the oral aperture.

The number and/or the shape of the projections, for example the height and/or the width of the projections, is preferably used as an identifier of the category of the spacer, in particular to determine its size. FIG. 8 shows three photographs acquired with the mobile telephone, in the service position, with three different spacers. Each spacer carries a different number of projections, the number of projections depending on the dimensions of the spacer that is used.

For example, the number of projections may be 4 for the size S (small; FIG. 8A) suitable for children, 2 for the size M (medium; FIG. 8B) and 0 for the size L (large; FIG. 8C). The projections 43 are preferably distributed regularly along the contour of the oral aperture.

The projections 43 are visible, very partially masking the oral aperture. Their dimensions make it possible not to impede the interpretation of the photographs.

In one embodiment illustrated in FIG. 10, the shown first mark, preferably a categorization mark, is a luminous mark shown in the view observed by the optical lens. The luminous mark may in particular be generated by light passing through one or more through-holes formed through the spacer and/or the adapter, or by light passing through a region of the support exhibiting a local reduction in thickness, as illustrated in FIG. 11, or exhibiting a particular color, or a particular composition or a particular microstructure.

Advantageously, the shown first mark does not, even partially, mask the user's face, and in particular the user's teeth, in the view observed by the optical lens.

The first identifier may be determined by the shape and/or by a characteristic of the light of the luminous mark. This shape and this characteristic of the light may in particular result from the shape and/or the area of one or more of the holes and/or the number of holes and/or the distribution of the holes.

In one embodiment, the kit comprises multiple removable spacers, referenced $\mathbf{24}_1$ and $\mathbf{24}_2$ in FIG. 7, which are able to be joined to the adapter 26 and have oral apertures and/or carry different personalization marks and/or categorization marks.

Two spacers of the kit may differ in terms of the personalization mark. Advantageously, two spacers of the same size may thus identify different people. In addition, the adapter may be used for multiple spacers, for example each assigned to a child of a sibling.

In one embodiment, the kit comprises multiple removable spacers of different shapes that are able to be joined to the adapter 26 and carry different respective categorization marks. Advantageously, the adapter 26 may be used for multiple different spacers, for example adapted to different pathologies or to different users, the categorization marks facilitating the choice of a spacer depending on the situation.

Controller

The controller 21 is a computerized processing device programmed to read and analyze a personalization mark and/or a categorization mark, and then accordingly to

- record and/or transmit information prepared on the basis of the analysis, for example to inform the user and/or modify the calibration of the mobile telephone, and/or authorize triggering of an acquisition of a 2D or 3D representation.

The controller 21 comprises in particular a processor and a computer memory, and preferably a human-machine interface conventionally comprising a screen and a module for communicating via the Internet, via Wi-Fi, via Bluetooth® or via the telephony network. A computer program, comprising code instructions for commanding the reading of a shown mark, interpreting it so as to determine an identifier, and acting accordingly, is loaded into the memory of the controller 21. Preferably, this program allows the controller to compare the identifier with a setpoint, and to act on the basis of the score resulting from the comparison.

In one preferred embodiment, the controller 21 is integrated into the mobile telephone. As an alternative, it may be partially in the mobile telephone and partially in a remotely available computer in communication with the mobile telephone. The remote computer may advantageously have computer processing and/or data storage capabilities greater than those of the mobile telephone.

The controller 21 may process an "acquirable" view before the acquisition, for example process the 2D image shown on the screen of the mobile telephone before it is acquired, that is to say recorded by the mobile telephone. The check thus makes it possible to guide the user with regard to the acquisition, before the acquisition itself, for example by informing the user before they trigger the camera of the mobile telephone.

The controller 21 may process an "acquired" view, for example process a 2D image recorded in a memory of the mobile telephone.

The check is preferably carried out in real time, and for example starts less than 5 seconds after generation of the view, thereby making it possible to inform the user, for example so that they change spacer if it is not adapted to their morphology.

When the mark read by the controller 21 provides only an indirect identifier, a database, for example a correspondence table, may be loaded into the memory of the controller 21 so as to determine a direct identifier based on the indirect identifier. The controller 21 may determine the direct identifier based on additional information, for example based on a correspondence table with two or more entries establishing a link between a direct identifier and the indirect identifier.

To carry out step 1), the controller 21 comprises a reader designed to read the shown first mark, for example a barcode reader if the shown first mark is in the form of a barcode.

In one embodiment, the reader first places a first neural network specializing in locating and detecting objects in an image in order to isolate the shown first mark, and then a second neural network specializing in image classification so as to read the identifier provided by the shown first mark.

The neural networks are preferably chosen from the above lists.

The first neural network preferably proceeds according to the following steps:

- creating a learning base comprising more than 1000, preferably more than 10 000 and/or fewer than 1 000 000 historical structures, each historical structure comprising
  - a "historical" view acquired with a support according to the invention and showing a "historical" mark, and
  - a "historical" extract from said historical view showing the historical mark in isolation,
- training the neural network by way of the learning base, preferably by providing said historical views at input of the neural network and said historical extracts at output;
- submitting the view showing the shown first mark, at input of said trained neural network, such that it provides an extract of said view showing said shown first mark in isolation.

The second neural network preferably proceeds according to the following steps:

- creating a learning base comprising more than 1000, preferably more than 10 000 and/or fewer than 1 000 000 historical structures, each historical structure comprising
  - a "historical" extract, and
  - a "historical" identifier for the historical mark shown in the historical extract,
- training the neural network by way of the learning base, preferably by providing said historical extracts at input of the neural network and said historical identifiers at output;
- submitting the extract of said view showing said shown first mark in isolation, at input of said trained second neural network, such that it determines an identifier for said shown first mark.

In one preferred embodiment, a single neural network specializing in locating and detecting objects in an image, "Object Detection Networks", is used, for example R-CNN (2013), SSD (Single Shot MultiBox Detector: Object Detection network), Faster R-CNN (Faster Region-based Convolutional Network method: Object Detection network), Faster R-CNN (2015), or SSD (2015).

The shown first mark may in particular be a categorization mark providing an identifier of the size of the spacer, for example "S", "M" or L.

If the identifier determined by the controller 21 is insufficient to immediately determine the category to be identified, it deduces an identifier sufficient for this purpose, based on additional information, as indicated above. The additional information may be partially or fully provided by the user. For example, the controller may present the identifier determined by the controller to the user and ask the user to accordingly determine and then enter said sufficient identifier. Preferably, the additional information is available in a database to which the controller has access. The controller is thus able to identify, directly or indirectly, a category based on the identifier that it has read.

In step 2), the controller may inform the user about the identified category, preferably by sending a message on the screen of the mobile telephone. For example, it may display a message indicating the size of the spacer so that the user is able to check whether the spacer is suitable for them. It may also inform a dental professional.

It may modify the calibration of the mobile telephone to adapt it to the category, for example to adjust the zoom according to the size of the spacer.

It may modify a record of the 2D or 3D representation so as to associate it with the category, in order to improve subsequent processing of said representation.

Finally, it may authorize triggering of an acquisition of the 2D or 3D representation.

In one preferred embodiment, the controller checks, on the basis of the identified category, that the situation complies with an acceptable situation, called "setpoint situation".

A setpoint situation is a situation in which the adapter, the spacer and the mobile telephone are technically compatible with one another, with the calibration, and with the user (for example with the size of their mouth or with a particular comfort level).

Preferably, the controller searches for a setpoint before checking whether said category complies with the setpoint.

As illustrated in the various applications that follow, the setpoint for a categorization mark or a personalization mark may be

- entered by the user or deduced from a datum entered by the user;
- deduced from the view that the optical lens has.

The controller may ask the user to inform it about the setpoint. For example, it may ask the user their age in order to determine the size of a spacer suitable for their age.

In one embodiment, the controller 21 determines, based on a second identifier provided by a shown second mark, in the form of a personalization mark, and possibly by consulting a database, information about the user, for example an identifier of the user, for example their name, and/or an identifier of their medical records, and/or their pathology and/or their treatment, and/or of a dental professional's practice and/or of a dental company, for example a group of dental professionals. It then determines the setpoint based on this information.

In one embodiment, the controller 21 determines, based on a second identifier provided by a shown second mark, in the form of a categorization mark, and possibly by consulting a database, information about another part of the kit different from the first component part. The database may in particular provide identifiers of the "other" parts that are technically compatible with the first component part.

In one embodiment, the controller 21 determines the setpoint based on information that the mobile telephone provides thereto, and possibly by consulting a database. The information provided by the mobile telephone may be for example the model of the mobile telephone or a calibration parameter of the mobile telephone, for example a focal length. The controller 21 may then determine a spacer size adapted to this information by consulting a database.

In the event of incompatibility with the setpoint, the controller preferably sends a message to the user, preferably via the screen of the mobile telephone, so that they change the spacer or the adapter or modify the acquisition conditions, and then repeat the acquisition operation. The categorization mark and/or the personalization mark thus allow an "embedded check" during the acquisition.

Preferably, if a 2D or 3D representation has been acquired under conditions that do not comply with the setpoint, for example with an unsuitable spacer or a spacer in an unsuitable calibration, the controller 21 deletes it.

Exemplary Applications

Comparison of Identifiers with One Another

The categorization and/or personalization marks may be used by the controller 21 to check that:

- the spacer that is used is compatible with the adapter that is used, by comparing the categories identified based on the categorization marks carried by the joined spacer and adapter; and/or
- the spacer or adapter that is used, identified by a categorization mark of said spacer or adapter, is compatible with the person identified by a personalization mark carried by the spacer or by the adapter; and/or
- the person identified by a personalization mark carried by the spacer is compatible with the person identified by a personalization mark carried by the adapter.

The controller 21 may use a database to check said compatibility. The database may in particular associate a spacer category with an adapter category, or a person with a spacer category, or a person with an adapter category.

Comparison of an Identifier with Information Specific to the User

Beyond the information that the controller 21 is able to deduce from the personalization marks 39 or categorization marks 41 or 41', the controller 21 is preferably also programmed to determine, based on the view, preferably based on the representation in said view of the user's mouth, information specific to the user.

The information specific to the user may be determined from reading of an oral mark affixed to the user's mouth, in particular to the user's teeth, for example a mark, for example in the form of a dot, glued to a tooth of the user or to an orthodontic appliance worn by the user, as explained above.

The information specific to the user might not be reported and may be deduced from the representation of the teeth and/or the gums and/or the lips and/or the teeth in the view that the optical lens has. For example, it may be deduced from the shape of one or more teeth, from the relative arrangement of multiple teeth, from a size of the mouth, for example the width of a jaw. A dimension may be deduced in particular from a comparison with a dimension of the spacer able to be measured in the view.

The controller 21 may then compare the information specific to the user with the information specific to a plurality of people in order to identify, among these people, the person whose information specific to the user best matches that of the user. For example, the controller 21 may compare the shape and/or the arrangement of the teeth in the view that the optical lens has with the shape and/or the arrangement of the teeth in 3D models of dental arches of various people, in order to identify the user among those people.

In particular, the information specific to the user may be determined by way of a neural network.

The neural network is preferably a network specializing in image classification, preferably chosen from the above list.

The procedure is preferably carried out according to the following steps:

- creating a learning base comprising more than 1000, preferably more than 10 000 and/or fewer than 1 000 000 historical structures, each historical structure comprising
  - at least one view, called "historical view", preferably acquired with a support of a kit according to the invention in the service position, at least partially showing the mouth of at least one "historical" person, and
  - information specific to the "historical" person, or "historical information",
- training the neural network by way of the learning base, preferably by providing said historical views at input of the neural network and said historical information at output;
- submitting the view showing said shown first mark, at input of said trained neural network, such that it determines information specific to the user using the kit.

The information specific to a historical person may be in particular their age or the size of their jaw or their mouth, and for example take a value from among "child's mouth", "medium-sized adult's mouth" or "large adult's mouth", or equivalent values.

To improve the quality of the specific information that is obtained, it is preferable to use

- first of all, a first neural network similar to the first neural network described above, but trained to extract the portion of said view that contains the specific information, for example in order to extract the representation of multiple predetermined adjacent teeth, and then
- the neural network described in the above two paragraphs but trained with the historical extracts instead of the historical views, the extract of said view that contains the information specific to the user being submitted at input of said trained second neural network (and no longer said view itself).

The portion of the view that contains the specific information may be in particular a representation of the teeth. Indeed, since each person has a set of teeth specific to them, analyzing the representation of the teeth makes it possible to identify the user who has used the kit.

In one embodiment, this analysis is carried out by the controller 21, preferably

- by comparing the representation of the teeth in the view with digital three-dimensional models of the sets of teeth of a set of people, for example generated by way of an optical scanner, and then
- by selecting the person whose digital three-dimensional model best matches (or "best fits") said representation of the teeth in said view. The information specific to this person may then be assigned to the user, the user being identified by the identifier of said person.

The search for the digital three-dimensional model that best corresponds to said representation of the teeth may in particular be carried out by a metaheuristic method, for example chosen from the above list.

The controller may then determine the setpoint based on the information specific to the user.

Comparison of an Identifier with the Calibration of the Mobile Telephone

The mobile telephone knows the values of the parameters of the calibration that is used, that is to say that are in force or "active". This information is preferably used by the controller 21 to check that the calibration in force is adapted to the spacer and/or to the adapter.

In particular, reading a categorization mark carried by the spacer that is used allows the controller 21 to check, for example in a database, whether the size of the spacer, determined based on the categorization mark, is adapted to the calibration that is used. In particular, the calibration in force may define an "active" depth of field. The database may associate a spacer category with a range of setpoint depths of field, for example depending on the size of the spacer. The controller 21 may then determine whether the active depth of field belongs to said range.

If the spacer does not belong to a category adapted to the calibration that is used, the controller 21 preferably modifies the calibration so that the new calibration is adapted to the spacer and/or sends a message to the user, preferably on their mobile telephone, for example to ask them to change spacer and/or to indicate a suitable spacer to said user, and/or deletes the representation acquired with the configuration that is used.

Comparison of an Identifier with the Model of the Mobile Telephone

The spacer and/or the adapter, in particular the adapter, may be incompatible with the model of the mobile telephone. For example, the adapter may be poorly adapted for the mobile telephone that is used to be attached securely thereto.

The model of the mobile telephone that is used, for example the fact that the mobile telephone that is used is an iPhone® 13, is known to the controller 21. The controller 21 is therefore able to check that it is adapted to the spacer and/or to the adapter.

In particular, reading a categorization mark carried by the adapter that is used allows the controller 21 to check, for example in a database, whether the attachment of the adapter intended to attach the mobile telephone, determined based on the categorization mark, is adapted to the model of the mobile telephone that is used. In particular, the database may associate an adapter category with one or more mobile telephone models.

If the adapter does not belong to a category adapted to the model of the mobile telephone that is used, the controller 21 preferably sends a message to the user, preferably on their mobile telephone, for example to ask them to change adapter, and/or deletes the representation acquired with the adapter that is used.

Operation

The operation of the kit follows directly from the above description.

Initially, the kit is in the disassembled position. If necessary, the user chooses a spacer 24 from among multiple spacers.

They clip the spacer 24 onto the adapter 26, inserting the end of the spacer 24 opposite the oral aperture Oa inside the receptacle of complementary shape defined by the adapter. The clipping preferably results from claws of the adapter being hooked into recesses formed on the outer surface of the spacer 24.

After clipping, the spacer and the adapter together define the chamber 28.

The user then grips the mobile telephone 12 between the first and second jaws such that the observation aperture Oa is substantially facing the lens 16, and preferably the flash. The kit, in the acquisition position, is then ready for use.

The user then inserts the distal rim 46 between their lips and their teeth and positions the oral aperture facing the teeth for which they wish to acquire one or more 2D or 3D representations, preferably take photographs or acquire a scan. It is then in a service position.

By pressing the trigger of the mobile telephone, the user acquires a 2D or 3D representation.

The view observed by the lens before the acquisition ("acquirable view") or recorded following the acquisition ("acquired view") is analyzed by the controller 21 in order to check that it is observed or has been acquired, respectively, in a situation compliant with a setpoint situation.

The setpoint situation defines a set of prescriptions involving one or more identifiers provided by one or more categorization marks and/or one or more personalization marks, and possibly information specific to the user and/or a calibration parameter and/or information about the model of the mobile telephone.

In particular, a categorization mark, for example in the form of one or more projections 43 (FIG. 8), may identify the size of the spacer, for example M. The setpoint may be provided by a database indicating, for each person, a suitable spacer size. The controller then searches, based on an identifier of the user performing the acquisition, for the corresponding size, constituting the setpoint.

The identifier of the user may be entered by an operator or, preferably, determined by the controller, as described above. The identifier of the user may then be used by the controller to search for the setpoint in a database giving a setpoint for each person.

As an alternative, in one embodiment, the setpoint is determined directly based on the acquirable or acquired view, and in particular by the representation of the teeth in this view, without it being necessary to determine the identifier of the user beforehand. For example, the size of the suitable spacer is determined by evaluating the jaw size measured directly in the representation.

The setpoint is for example the information that a spacer of size "S" should be used for the user.

The setpoint thus makes it possible to check that the spacer that is used, identified based on the categorization mark, is suitable for the user. In the above example, the categorization mark indicates that a spacer of size "S" should be used, but that it is a spacer of size "M" that is used. The comparison preferably leads to the user being warned to change spacer, and then acquire a new 2D or 3D representation and/or leads to the 2D or 3D representations acquired in a situation not compliant with the setpoint situation being deleted from the memory of the controller 21.

If necessary, the user then moves the oral aperture so as to acquire 2D or 3D representations with other orientations of the mobile telephone with respect to the user's teeth. In particular, by rotating the kit around them, the user allows the mobile telephone to observe different regions of their mouth, for example to take photographs of the dental arch or the teeth at the back of the mouth.

Preferably, the user acquires 2D or 3D representations by acquiring at least one front-on view, one right view and one left view.

The spacer does not prevent the user's jaws from moving toward or being spread from one another. It thus makes it possible to acquire in particular photographs showing the user's teeth, while the user has their mouth open or their mouth closed, keeping the lips rolled up.

Preferably, the user acquires 2D or 3D representations by acquiring at least one view with their mouth open and at least one view with their mouth closed, preferably each time for front-on, right and left views.

The user then removes the spacer 24 from their mouth and disassembles the mobile telephone.

The controller may then analyze the acquired representation and/or transmit it with the mobile telephone 12. Finally, the user separates the spacer 24 from the adapter 26 in order to clean it.

Of course, the order of the operations may be modified. For example, the user may attach the spacer to the adapter before or after attaching the mobile telephone. The dismantling of the spacer may be earlier or later than that of the mobile telephone.

As is now clearly apparent, the invention limits the risk of acquiring photographs or 3D models in a non-compliant situation, and in particular with a spacer unsuitable for the user, or with an adapter unsuitable for the mobile telephone or the spacer, or with a mobile telephone the calibration of which is not adapted to the spacer.

The kit allows fast acquisition, under excellent hygiene conditions, typically in less than one minute, without the need for a specialized person, in particular a dentist or an orthodontist. The acquisition may be carried out in particular by the user themselves or by one of their relatives, with a simple mobile telephone, anywhere, and in particular outside a medical, dental or orthodontic practice. In addition, the acquisition is possible without the use of a tool resting on the ground in order to immobilize the mobile telephone, and in particular without a tripod.

Finally, the kit allows fast and secure attachment of the mobile telephone, regardless of its thickness, without the risk of damaging it. It may be implemented as part of the method described in PCT/EP2015/074896.

Of course, the invention is not limited to the embodiments described and shown, which are provided for illustrative purposes only.

In particular, the shape of the spacer is not limiting. In particular, in one embodiment, the chamber opens out only via the oral and observation apertures. However, this embodiment is not limiting, and the chamber may comprise other apertures.

The invention claimed is:

1. An acquisition kit comprising:

a mobile telephone equipped with an optical lens for acquiring a 2D representation and/or a 3D representation;

a support to which the mobile telephone is attached, the support defining an oral aperture intended to be inserted into the mouth of a user, the optical lens having a view at least partially showing the oral aperture, said view showing at least one first mark, called "shown first mark", chosen from among:

a categorization mark identifying a category to which a first component part of the support belongs, and/or a personalization mark identifying the user and/or a pathology of the user and/or a dental professional and/or a group of dental professionals, the kit comprising a computerized controller programmed so as to 1) Read the shown first mark and deduce therefrom a first identifier, and then, 2) Record the first identifier, and/or prepare a message on the basis of the first identifier and transmit it to the user and/or to a dental professional, and/or modify the calibration of the mobile telephone on the basis of said first identifier, wherein the support comprises a spacer opening out via the oral aperture and/or an adapter attached to the spacer.

2. The acquisition kit as claimed in claim 1, wherein the categorization mark is arranged such that, in the view observed by the optical lens, it projects toward the inside of the representation of the oral aperture over a height greater than 0.01/10 and less than 1/10 of the largest dimension of the oral aperture.

3. The acquisition kit as claimed in claim 2, wherein the categorization mark comprises one or more projections, the number and/or the shape of the projections constituting an identifier of the category of said component part.

4. The acquisition kit as claimed in claim 3, wherein the one or more projections extend in the extension of the oral aperture.

5. The acquisition kit as claimed in claim 1, wherein the categorization mark is a luminous mark resulting from light passing through a wall of the support.

6. The acquisition kit as claimed in claim 1, wherein said category defines a size of the first component part.

7. The acquisition kit as claimed in claim 1, wherein the controller is programmed so as to in step 2), display, on a screen of the mobile telephone, information relating to the category identified by the first identifier, or after step 1) and prior to step 2), compare the first identifier with a setpoint so as to determine a score, and then execute step 2) on the basis of the score.

8. The acquisition kit as claimed in claim 7, wherein the setpoint is chosen from the group consisting of:

a second identifier deduced by virtue of the controller reading a second mark shown in said view, information specific to the user, an identifier of the model of the mobile telephone or a calibration parameter of the mobile telephone, a normative reference, a setpoint derived from said second identifier and/or from said information specific to the user and/or from said identifier of the model of the mobile telephone and/or from said calibration parameter of the mobile telephone and/or from said normative reference.

9. The acquisition kit as claimed in claim 8, wherein said shown first mark is carried by the first component part, and wherein the controller is configured to determine the setpoint based on a so-called second identifier provided by a shown second mark carried by a second component part of the support, joined removably to the first component part.

10. The acquisition kit as claimed in claim 8, wherein the controller is configured, when the oral aperture is in the user's mouth and user's teeth are visible to the optical lens, to determine said information specific to the user from said view.

11. The acquisition kit as claimed in claim 8, wherein the controller is configured to search in a database referencing a plurality of people for a person compatible with the representation of teeth in said view, and then determine the information specific to the user based on data in relation to said person.

12. The acquisition kit as claimed in claim 8, wherein the support comprises a spacer opening out via the oral aperture, an adapter removably attached to the spacer and defining, with the spacer, a chamber opening out via the oral aperture and via an observation aperture through which the optical lens has said view, the adapter comprising a base to which the mobile telephone is rigidly and removably attached, in which kit:

the first identifier designates a spacer category, said setpoint designates an adapter category, and the controller is programmed to deduce said first identifier from a categorization mark carried by the spacer and, preferably, to deduce said setpoint from a categorization mark carried by the spacer, and then, preferably, to check, based on the score, the compatibility between the spacer and the adapter; or the first identifier designates an adapter category, the setpoint designates a mobile telephone category, and the controller is programmed to deduce said first identifier from a categorization mark carried by the adapter, and then, preferably, to check, based on the score, the compatibility between the mobile telephone and the adapter; or the first identifier designates a spacer category, the setpoint designates a value of a parameter of the calibration of the mobile telephone, and the controller is programmed to deduce said first identifier from a categorization mark carried by the adapter, and then, preferably, to check, based on the score, the compatibility between the calibration of the mobile telephone for acquiring the 2D and 3D representation and the spacer and preferably, in the event of incompatibility, to modify the calibration of the mobile telephone on the basis of said score; or the first identifier designates a spacer category, the setpoint designates a spacer category derived from the information specific to the user, and the controller is programmed to deduce said first identifier from a categorization mark carried by the spacer, and preferably to determine, based on the score obtained, whether the spacer is technically compatible with the user;

the first identifier designates a spacer or adapter category, the setpoint designates a prescription set by a state or a company, and the controller is programmed to deduce said first identifier from a categorization mark carried by the support, and then, preferably, to check, based on the score, the compatibility between the spacer or the adapter, respectively, and said prescription.

13. The acquisition kit as claimed in claim 12, comprising, in addition to the spacer attached to the adapter, at least one other spacer able to be joined to the adapter, different from the spacer attached to the adapter and carrying a said shown mark different from that carried by the spacer attached to the adapter.

14. A method for acquiring a 2D or 3D representation by way of an acquisition kit as claimed in claim 1, said method comprising the following steps:

a) the user partially inserting the support into the user's mouth such that the optical lens of the mobile telephone has a view of the user's teeth through the oral aperture, spreading the user's lips so as to reveal said teeth;

b) activating the mobile telephone so as to acquire said 2D or 3D representation;

c) modifying the positioning of the oral aperture relative to the user, for example by rotation about the user, and then returning to step b), the controller executing a series of steps 1) and 2) at at least one checking time.

15. The method as claimed in claim 14, wherein at least one so-called representation facing the user and at least one so-called representation to the right or to the left of the user are acquired.

16. A method for acquiring a 2D or 3D representation by way of an acquisition kit as claimed in claim 1, said method comprising the following steps:

a) the user partially inserting the support into the user's mouth such that the optical lens of the mobile telephone has a view of the user's teeth through the oral aperture, spreading the user's lips so as to reveal said teeth;

b) activating the mobile telephone so as to acquire said 2D or 3D representation; c) modifying the positioning of the oral aperture relative to the user, for example by rotation about the user, and then returning to step b), the controller executing a series of steps 1) and 2) at at least one checking time and wherein the controller informs the user of said score in real time via the mobile telephone.

* * * * *